US00PP23140P2

(12) United States Plant Patent
van Dijk

(10) Patent No.: US PP23,140 P2
(45) Date of Patent: Oct. 23, 2012

(54) ***ANTHURIUM* PLANT NAMED 'ANTHZUPAP'**

(50) Latin Name: ***Anthurium andreanum* L.**
Varietal Denomination: Anthzupap

(75) Inventor: Jan van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 13/066,330

(22) Filed: Apr. 12, 2011

(51) Int. Cl.
*A01H 5/00* (2006.01)

(52) U.S. Cl. ..... Plt./365

(58) Field of Classification Search ..... Plt./365
See application file for complete search history.

*Primary Examiner* — Kent L Bell

(74) *Attorney, Agent, or Firm* — Jondle & Associates, P.C.

(57) ABSTRACT

A new *Anthurium* plant particularly distinguished by having glossy orange-red, durable spathes that slowly turn brown with age, dark green, durable leaves, an erect penduncle, rich shoot formation, flowers continuously throughout the year, a compact and full plant habit and a plant height of 35.0 cm to 45.0 cm, is disclosed.

3 Drawing Sheets

Genus and species: *Anthurium andreanum* L.
Variety denomination: 'Anthzupap'.

BACKGROUND OF THE NEW PLANT

The present invention comprises a new and distinct variety of *Anthurium*, botanically known as *Anthurium andreanum* L., and hereinafter referred to by the variety name 'Anthzupap'. The new variety originated from a hybridization made in April 2002 in Bleiswijk, The Netherlands. The female parent was a dark red *Anthurium* pot plant '4431-01' (unpatented), while the male parent was a red *Anthurium* plant '4462-07' (unpatented).

A single plant was selected in February 2004 and has been asexually reproduced repeatedly by tissue culture in Bleiswijk, The Netherlands over a five-year period. The new variety has been found to retain its distinctive characteristics through successive asexual propagations.

Plant Breeder's Rights for this variety were applied for in the European Union on Dec. 8, 2008 and in Japan on Mar. 9, 2010. 'Anthzupap' has not been made publicly available more than one year prior to the filing of this application.

SUMMARY OF THE INVENTION

The following are the most outstanding and distinguishing characteristics of this new variety when grown under normal horticultural practices in Bleiswijk, The Netherlands.

1) An orange-red colored medium sized glossy spathe;
2) White spadix;
3) Rich shoot formation;
4) Compact plant habit; and
5) Dark green foliage.

DESCRIPTION OF THE PHOTOGRAPHS

This new *Anthurium* plant is illustrated by the accompanying photographs; the colors shown are as true as can be reasonably obtained by conventional photographic procedures. The photographs are of a 48-week old plant grown in a greenhouse in Bleiswijk, The Netherlands in 2009.

DESCRIPTION OF THE NEW VARIETY

Figure 1:
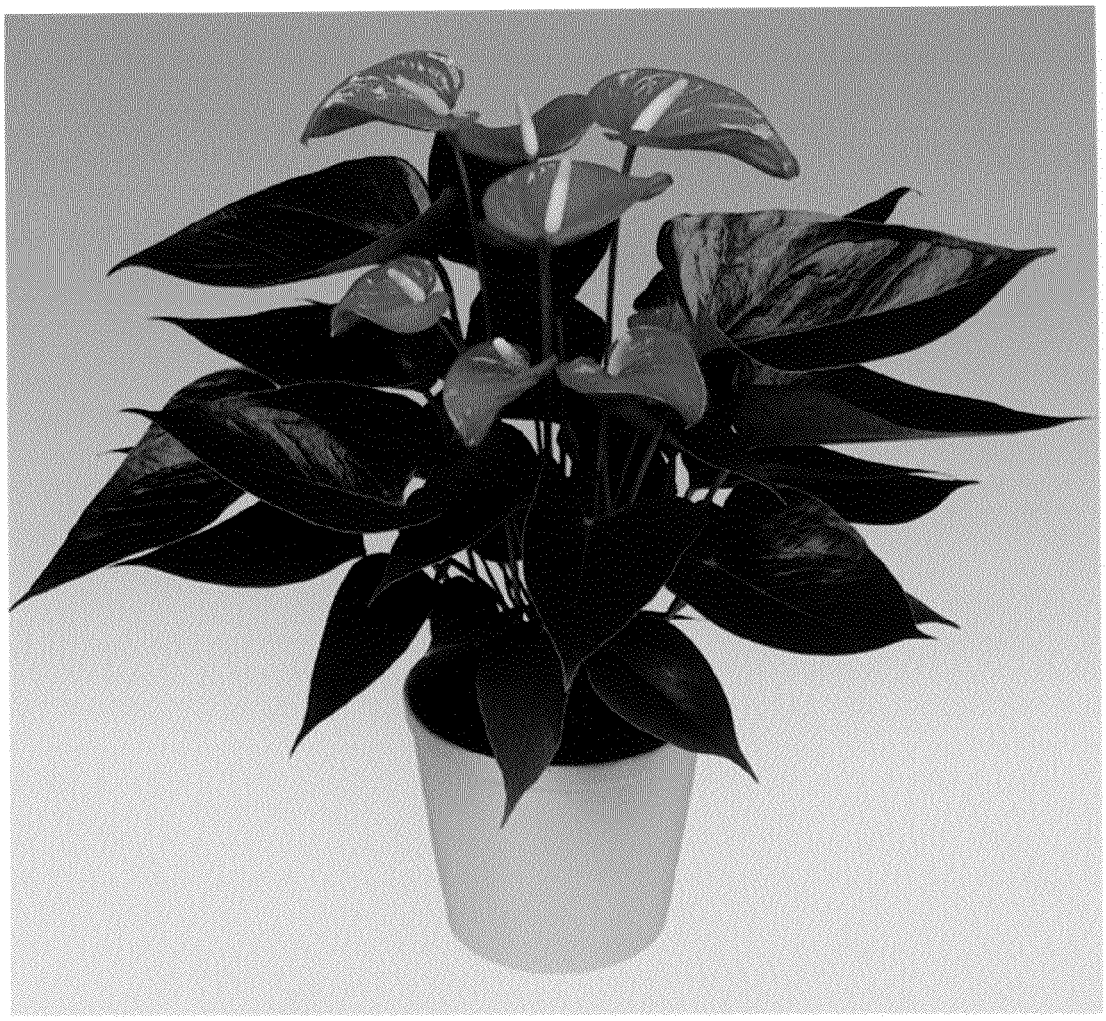
FIG. 1 shows the overall plant habit, including blooms, buds and foliage.
Figure 2:
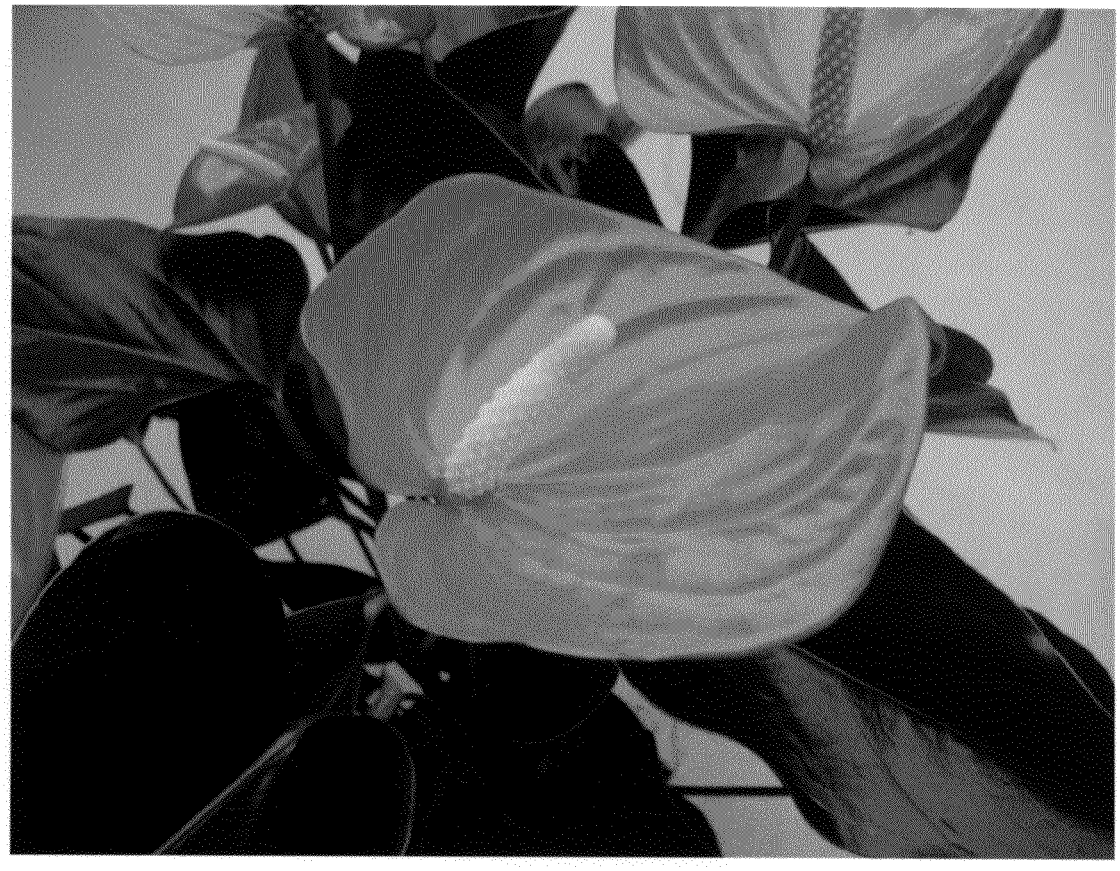
FIG. 2 is a close-up of the mature spathe.
Figure 3:
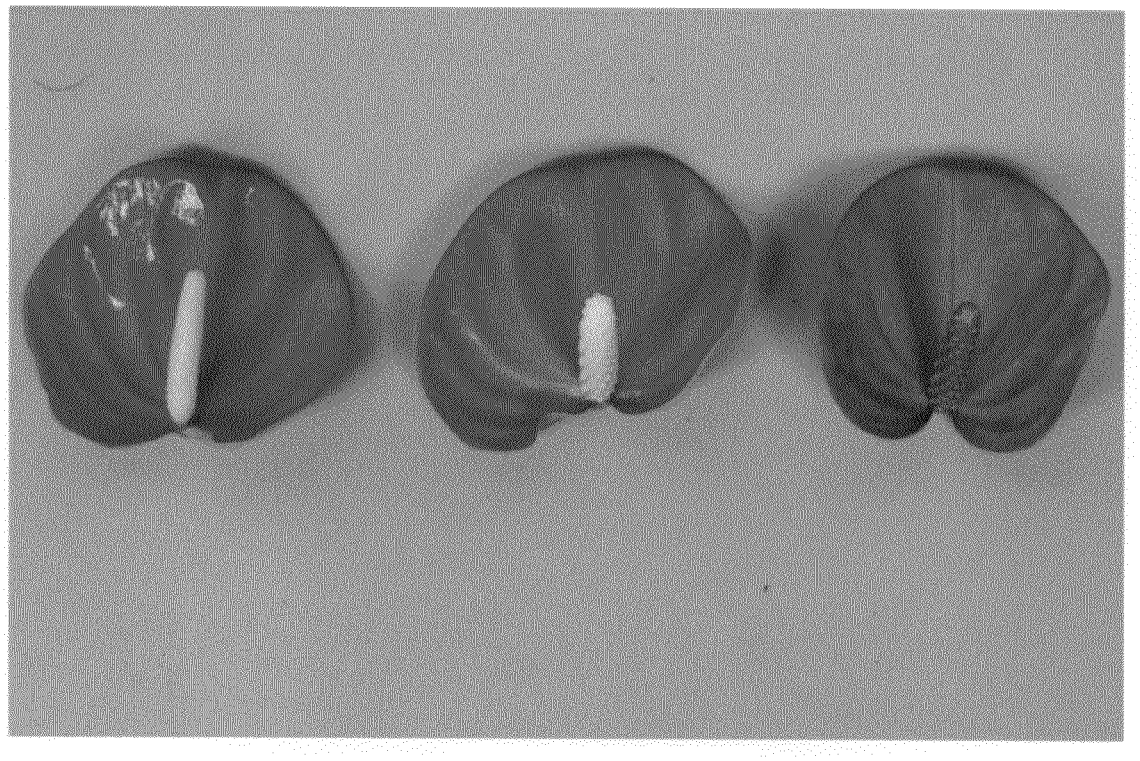
FIG. 3 shows three spathes at different stages of development.
Figure 4:
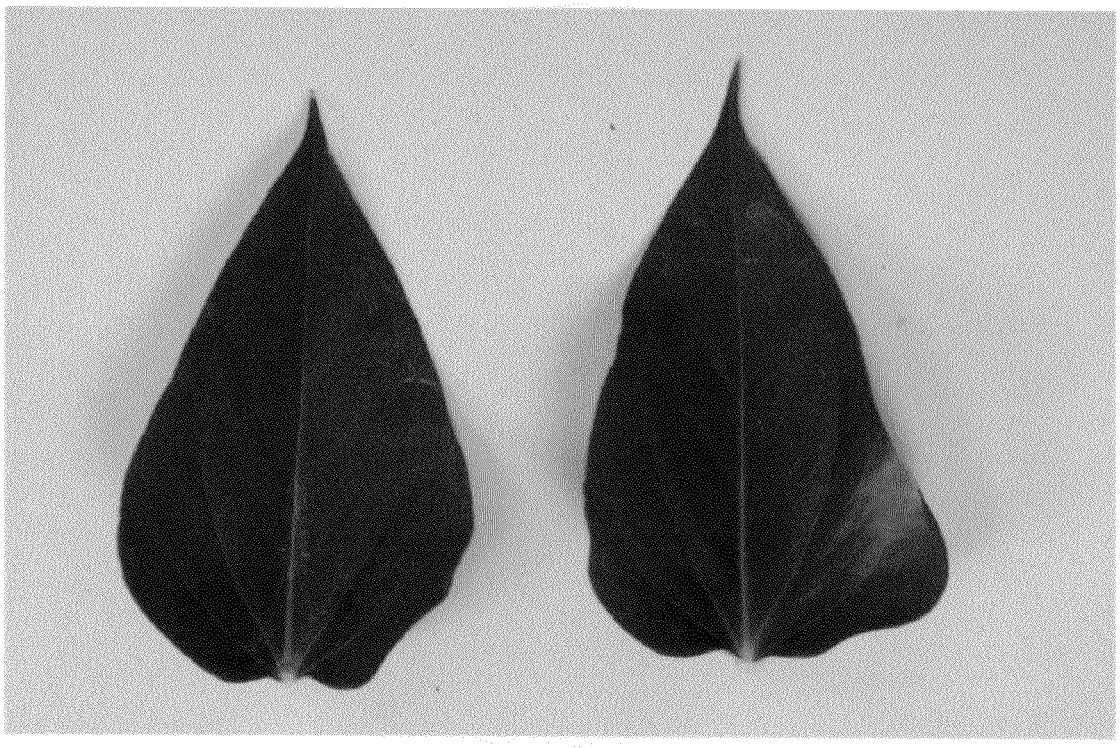
FIG. 4 shows the upper and lower leaf surfaces.

The following detailed description sets forth the distinctive characteristics of 'Anthzupap'. The data which define these characteristics were collected from asexual reproductions carried out in Bleiswijk, The Netherlands. The plant history was taken on 48-week old plants which were planted from tissue culture in 17 centimeter pots and grown in a glass greenhouse between 19° C. and 24° C. Observations were made in November of 2009. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:
- *Family*.—Araceae.
- *Botanical*.—*Anthurium andreanum* L.
- *Common name*.—*Anthurium*.

Parentage:
- *Female parent*.—*Anthurium* plant '4431-01' (unpatented).
- *Male parent*.—*Anthurium* plant '4462-07' (unpatented).

Plant:
- *Propagation*.—Tissue culture.
- *Root description*.—Fleshy cream-colored roots with smaller hairy lateral roots having yellow-colored root tips.
- *Time to produce a finished flowering plant*.—50 to 55 weeks for a 17.0 cm pot.
- *Growth habit*.—Herbaceous perennial.
- *Height* (*measured from soil, including inflorescence*).—35.0 cm to 45.0 cm.
- *Width* (*measured from leaf tips*).—50.0 cm to 60.0 cm.

Leaves:

*Immature leaves*.—Length: 8.0 cm to 12.0 cm. Width: 4.0 cm to 7.0 cm. Color: Upper surface: RHS 137A. Lower surface: RHS 146A. Texture (on both surfaces): Shiny.

*Mature leaves*.—Length (fully expanded): 13.0 cm to 19.0 cm. Width: 8.0 cm to 12.0 cm. Shape: Ovate, cupped. Apex: Acuminate. Base: Subcordate. Leaf blade angle with the petiole: Between 110 degrees and 130 degrees. Leaf margin: Entire. Color: Upper surface: RHS 136A. Lower surface: RHS 137B. Texture: Shiny, leathery and thick; very little to no blistering (on both sides). Venation: Pinnate with protruding primary and mid-veins at the underside of the leaf blade. Venation color: Upper surface: RHS 137C. Lower surface: RHS 147C.

*Lobes*.—Arrangement: Leaf blade has two large lobes extending past the petiole. Length of lobes of mature leaf blades: 0.5 cm to 1.5 cm. Width of lobes of mature leaf blades: 5.0 cm to 6.0 cm. Distance for petiole/leaf junction to highest point on lobes of mature leaf blades: 3.0 cm to 4.5 cm.

*Petiole*.—Cross-section: Round. Diameter: 0.3 cm to 0.5 cm. Length: 18.0 cm to 26.0 cm for a mature leaf size. Color: Mature leaf: RHS 146B. Immature leaf: RHS 146B. Cataphyl color surrounding the petiole: Outside: RHS 146C. Inside: RHS 147C.

*Geniculum*.—Length: 1.5 to 2.5 cm. Width: 0.4 cm to 0.5 cm. Color: RHS 146A.

Inflorescence:

*Arrangement*.—Single.

*Flowering habit* (*length of flowering season*).—Continuous.

*Number of inflorescences per plant*.—6 to 10.

*Fragrance*.—Absent.

*Longevity of inflorescence on plant*.—Up to a year.

*Longevity of the flower as a cut flower*.—Not observed.

Spathe:

*Buds*.—The spathe is tightly rolled around the spadix and extrudes from the peduncle sheath. After the spathe is fully opened the peduncle elongates some extra centimeters.

*Arrangement*.—Spathe angle with the peduncle is between 90 degrees and 110 degrees; the spathe stands on a wiry peduncle about 3.0 cm to 6.0 cm above the foliage.

*Shape*.—Ovate slightly cupped.

*Apex*.—Acuminate.

*Base*.—Cordate.

*Texture*.—Shiny; slight blistering.

*Margin*.—Entire. The margin slightly curves downward.

*Size*.—Height: 18.0 cm to 30.0 cm (Peduncle length at maturity). Length: 8.0 cm to 11.0 cm. Width: 7.0 cm to 9.0 cm.

*Color*.—Just fully open: Upper surface: RHS 45B. Lower surface: RHS 45D. At 7 to 8 weeks after opening: The upper surface becomes RHS 45A, slowly turning brown (approximately RHS 181A) towards the lobes. At 14 to 16 weeks after opening: The color slowly turns brown completely originating from the lobes towards the tip. The primary color of the upper and lower surfaces has become brown by that time (approximately RHS 166A).

*Peduncle*.—Shape: Erect. Cross-section: Round. Length: 18.0 cm to 30.0 cm. Diameter: 0.2 cm to 0.4 cm. Color: RHS 146B at unrolling of spathe, slowly turning RHS 146A with some slight pigmentation up to RHS 176A on the peduncle when the spathe matures.

Flowering time:

*General*.—One small rooted untreated tissue culture plant of 2 cm tall will flower, depending on season, after 6 to 8 months and 2 to 3 blossoms appear. More blossoms appear after some additional weeks so that a full flowering and commercial plant will have 6 to 10 orange red spathes. Smaller blossoms may occur on less mature plants.

Spadix:

*Size*.—Length: 3.0 cm to 5.0 cm (depending on flower size). Width (at apex): 0.4 cm to 0.6 cm. Width (at base): 0.5 cm to 0.8 cm.

*Shape*.—Columnar.

*Angle of spadix tip with peduncle*.—180 degrees (spadix is in one line with peduncle).

*Texture*.—When the spathe is unfurling the spadix is smooth. When the spadix matures, very small stigmata protrude. The stigmata are evenly distributed round the spadix. The spadix matures from base to top, slowly giving the spadix a somewhat rough appearance.

*Color*.—Immature: RHS 15A. Mature: RHS 155A. Ages to: RHS 146A.

Flowers:

*Quantity per spadix*.—180 to 250.

*Spadix flower arrangement*.—Bisexual, rounded in cross-section.

*Shape*.—Rounded.

*Size*.—Length: 0.1 cm to 0.2 cm. Diameter (maximum): 0.2 cm.

*Color*.—RHS 155A.

Reproductive organs:

*Stamens*.—None visible.

*Pollen*.—Sparse.

*Pollen color*.—RHS 156D.

*Pistil*.—Quantity: Many. Length: Less than 0.01 cm. Color: RHS 155A.

*Style*.—None observed.

*Stigma*.—Shape: Ovoid. Diameter: Less than 0.01 cm. Color: RHS 155A.

*Ovary*.—Rarely visible.

*Ovary color*.—RHS 155A.

Fruit and seed set: None observed.

COMPARISON WITH PARENTAL AND COMMERCIAL VARIETYS

'Anthzupap' differs from the female parent '4431-01' (unpatented) by having orange-red spathes, whereas '4431-01' has dark red spathes.

'Anthzupap' differs from the male parent '4462-07' (unpatented), by having orange-red spathes, whereas '4462-07' has red spathes.

'Anthzupap' is comparable to commercially available varieties 'Anthuci' and 'Anthabazal'. 'Anthzupap' differs from 'Anthuci' in that 'Anthzupap' has slight spathe blistering, while 'Anthuci' has strong spathe blistering. Additionally, the mature leaf lobes of 'Anthzupap' are smaller than the leaf lobes of 'Anthuci'. 'Anthzupap' differs from 'Anthabazal' in that 'Anthzupap' has orange-red spathes, while 'Anthabazal' has red spathes.

TABLE 1

Comparison of characteristics between 'Anthzupap', 'Anthuci' and 'Anthabazal'

| Characteristic | 'Anthzupap' | 'Anthuci' | 'Anthabazal' |
|---|---|---|---|
| Plant height at maturity | 35.0-45.0 cm | 45.0-55.0 cm | 35.0-45.0 cm |
| Spathe blistering | Slight | Strong | Slight |

TABLE 1-continued

Comparison of characteristics between 'Anthzupap', 'Anthuci' and 'Anthabazal'

| Characteristic | 'Anthzupap' | 'Anthuci' | 'Anthabazal' |
|---|---|---|---|
| Length of lobes of mature leaf blades | 0.5-1.5 cm | 3.0-6.0 cm | 1.5-3.5 cm |
| Color of spathe | RHS 45B | RHS 45B | RHS 34A |

I claim:

1. A new and distinct variety of *Anthurium* plant named 'Anthzupap' as shown and described herein.

* * * * *